US012570985B2

(12) United States Patent
Wu et al.

(10) Patent No.: US 12,570,985 B2
(45) Date of Patent: Mar. 10, 2026

(54) XYLANASE MUTANT HAVING IMPROVED SPECIFIC ACTIVITY

(71) Applicant: QINGDAO VLAND BIOTECH GROUP CO., LTD., Qingdao (CN)

(72) Inventors: Xiuxiu Wu, Qingdao (CN); Rongxi Song, Qingdao (CN); Yijun Huang, Qingdao (CN)

(73) Assignee: QINGDAO VLAND BIOTECH GROUP CO., LTD., Qingdao (CN)

( * ) Notice: Subject to any disclaimer, the term of this patent is extended or adjusted under 35 U.S.C. 154(b) by 1119 days.

(21) Appl. No.: 17/619,599

(22) PCT Filed: May 15, 2020

(86) PCT No.: PCT/CN2020/090456
§ 371 (c)(1),
(2) Date: Dec. 16, 2021

(87) PCT Pub. No.: WO2020/253426
PCT Pub. Date: Dec. 24, 2020

(65) Prior Publication Data
US 2022/0380778 A1      Dec. 1, 2022

(30) Foreign Application Priority Data

Jun. 18, 2019    (CN) .......................... 201910524192.9

(51) Int. Cl.
*C12N 15/52*          (2006.01)
*C12N 15/81*          (2006.01)
(52) U.S. Cl.
CPC ........... *C12N 15/52* (2013.01); *C12N 15/815* (2013.01); *C12N 2330/51* (2013.01)
(58) Field of Classification Search
None
See application file for complete search history.

(56) References Cited

U.S. PATENT DOCUMENTS

| | | | |
|---|---|---|---|
| 6,682,923 B1 * | 1/2004 | Bentzien ................ | D21C 5/005 435/320.1 |
| 8,722,382 B1 | 5/2014 | Guo et al. | |
| 2020/0239865 A1 | 7/2020 | Wu et al. | |

FOREIGN PATENT DOCUMENTS

| | | |
|---|---|---|
| CN | 102757947 A | 10/2012 |
| CN | 104109660 A | 10/2014 |
| CN | 105039290 A | 11/2015 |
| CN | 106676086 A | 5/2017 |
| CN | 106834255 A | 6/2017 |
| CN | 109402091 A | 3/2019 |

OTHER PUBLICATIONS

CN106834255, WIPO Machine Translation, 8 pages (Year: 2017).*
International Search Report for PCT/CN2020/090456 mailed Aug. 12, 2020, ISA/CN.
Chen. Y.L. et al., Directed evolution to produce an alkalophilic variant from a Neocallimastix patriciarum xylanase. Canadian Journal of Microbiology, vol. 47, No. 12, Dec. 31, 2001.
Database Geneseq [Online] Sep. 6, 2018 (Sep. 6, 2018), "Multifunctional cellulase Neele mutant, SEQ ID 4.", retrieved from EBI accession No. GSP:BFL57664 Database accession No. BFL57664.
Database Geneseq [Online] Sep. 6, 2018 (Sep. 6, 2018), "Multifunctional cellulase Neele mutant R150K.", retrieved from EBI accession No. GSP:BFL57676, Database accession No. BFL57676.
Database Geneseq [Online] Sep. 6, 2018 (Sep. 6, 2018), "Multifunctional cellulase Neele mutant F165W.", retrieved from EBI accession No. GSP:BFL57679, Database accession No. BFL57679.
Cheng Ya-Shan et al: "Improving the catalytic performance of a GH11 xylanase by rational protein engineering", Applied Microbiology and Biotechnology, Springer Berlin Heidelberg, Berlin/ Heidelberg, vol. 99, No. 22,Jun. 19, 2015 (Jun. 19, 2015), pp. 9503-9510,XP036118647,ISSN: 0175-7598, DOI:10.1007/S00253-015-6712-0 [retrieved on Jun. 19, 2015].
The European Search Report issued on Jun. 12, 2023 for EP20827264.1.

* cited by examiner

*Primary Examiner* — Carla J Myers
(74) *Attorney, Agent, or Firm* — Yue Apex (Robert) Xu; Attorneys at Law, LLP

(57) ABSTRACT

Provided is a xylanase mutant having improved specific activity, comprising any one or more mutation sites of M78F, V143I, R148K, F163W, I177V, and V206L. The specific activity of the mutant is improved, the production cost of xylanase is reduced, and the mutant can be used in feed.

9 Claims, No Drawings
Specification includes a Sequence Listing.

SEQUENCE LISTING

```
<160> NUMBER OF SEQ ID NOS: 4

<210> SEQ ID NO 1
<211> LENGTH: 225
<212> TYPE: PRT
<213> ORGANISM: Neocallimastix

<400> SEQUENCE: 1

Gln Ser Phe Cys Ser Ser Ala Ser His Ser Gly Gln Ser Val Lys Val
1               5                   10                  15

Thr Gly Asn Lys Val Gly Thr Ile Gly Gly Val Gly Tyr Glu Leu Trp
            20                  25                  30

Ala Asp Ser Gly Asn Asn Ser Ala Thr Phe Tyr Ser Asp Gly Ser Phe
        35                  40                  45

Ser Cys Thr Phe Gln Asn Ala Gly Asp Tyr Leu Cys Arg Ser Gly Leu
    50                  55                  60

Ser Phe Asp Ser Thr Lys Thr Pro Ser Gln Ile Gly Arg Met Lys Ala
65                  70                  75                  80

Asp Phe Lys Leu Val Lys Gln Asn Ser Ser Asn Val Gly Tyr Ser Tyr
                85                  90                  95

Val Gly Val Tyr Gly Trp Thr Arg Ser Pro Leu Val Glu Tyr Tyr Ile
            100                 105                 110

Val Asp Asn Trp Leu Ser Pro Phe Pro Pro Gly Asp Trp Val Gly Asn
            115                 120                 125

Lys Lys His Gly Ser Phe Thr Ile Asp Gly Ala Gln Tyr Thr Val Tyr
    130                 135                 140

Glu Asn Thr Arg Thr Gly Pro Ser Ile Asp Gly Asp Thr Thr Phe Asn
145                 150                 155                 160

Gln Tyr Phe Ser Ile Arg Gln Gln Ala Arg Asp Cys Gly Thr Ile Asp
            165                 170                 175

Ile Ser Ala His Phe Asp Gln Trp Glu Lys Leu Gly Met Thr Met Gly
            180                 185                 190

Lys Leu His Glu Ala Lys Val Leu Gly Glu Ala Gly Asn Val Asn Gly
        195                 200                 205

Gly Ala Ser Gly Thr Ala Asp Phe Pro Tyr Ala Lys Val Tyr Ile Gly
    210                 215                 220

Asp
225

<210> SEQ ID NO 2
<211> LENGTH: 675
<212> TYPE: DNA
<213> ORGANISM: Neocallimastix

<400> SEQUENCE: 2
caaagtttct gtagttcagc ttctcactct ggacaaagtg taaaggtaac cggcaacaag      60
gttggaacta ttggtggtgt tggttacgaa ttatgggctg atagtggtaa taacagtgct     120
actttctatt ctgatggttc cttctcatgt actttccaaa atgctgggga ttacttatgt     180
cgtagtggtc tttctttcga tagtactaag accccatctc aaattggtcg tatgaaggct     240
gatttcaaac ttgtcaaaca aaatagttcc aatgttggtt attcctatgt tggtgtttac     300
```

-continued

```
ggttggacta gaagtccact tgtcgaatac tacattgtcg ataattggct tagcccattc     360
ccaccaggtg attgggttgg taacaagaag catggttctt tcactattga tggtgctcaa     420
tacactgttt atgaaaacac tcgtactggt ccatctattg atggtgatac caccttcaat     480
caatacttta gtattcgtca acaagctcgt gattgtggta ccattgatat ttctgctcac     540
tttgatcaat gggaaaagct tggtatgact atgggtaaat tacatgaagc caaggtttta     600
ggtgaagccg gtaacgttaa cggtggtgcc agtggtaccg ctgatttccc gtacgcaaag     660
gtttacattg gtgat                                                     675

<210> SEQ ID NO 3
<211> LENGTH: 34
<212> TYPE: DNA
<213> ORGANISM: Artificial Sequence
<220> FEATURE:
<223> OTHER INFORMATION: PT-F1

<400> SEQUENCE: 3
ggcgaattcc aaagtttctg tagttcagct tctc                                 34

<210> SEQ ID NO 4
<211> LENGTH: 37
<212> TYPE: DNA
<213> ORGANISM: Artificial Sequence
<220> FEATURE:
<223> OTHER INFORMATION: PT-R1

<400> SEQUENCE: 4
atagcggccg cttatcatta atcaccaatg taaacct                              37
```

XYLANASE MUTANT HAVING IMPROVED SPECIFIC ACTIVITY

CROSS REFERENCE TO RELATED APPLICATIONS

This application is a US National Phase application based upon PCT Application No. PCT/CN2020/090456 filed May 15, 2020, which claims the priority of Chinese patent application filed with Chinese Patent Office on Jun. 18, 2019, the application number is 201910524192.9, and title of the application is "Xylanase Mutant with Increased Specific Activity", the entire content of which is incorporated by reference in this application.

INCORPORATION OF SEQUENCE LISTING

The Sequence Listing that is contained in the file named "revised OP2120-US-0465_sequence listing" (date created: Oct. 9, 2025; file size: 3,721 bytes) filed by electronic submission is incorporated by reference herein.

FIELD

The present disclosure relates to the technical field of genetic engineering and protein modification, specifically to a xylanase mutant with improved specific activity.

BACKGROUND

Xylan is a kind of hybrid polypenta-carbon sugar, the main chain is connected by multiple xylopyranose through xylosidic bonds, and a variety of short substituents of different sizes are attached to the side chains. Xylan mainly exists in the secondary wall of plant cells, between lignin and other polysaccharides, and plays a connecting role. Xylan is an important component of plant hemicellulose. It accounts for one third of the total plant carbohydrates. It is the second most abundant renewable material resource after cellulose in nature. Xylan accounts for 7%-12% of dry matter weight in gymnosperms, and 15%-30% of dry matter weight in angiosperms. The main raw materials of livestock and poultry feed in China are derived from plants, such as corn, wheat, barley, etc., which all contain a certain amount of xylan. For example, arabinoxylan in wheat seed coat accounts for 66% of its total non-starch polysaccharides (NSPs), arabinoxylan and β-glucan in the aleurone layer accounted for 65% and 31% of the total NSPs, respectively. 88% of the NSPs in endosperm cells are arabinoxylans, of which ⅓ are soluble. In actual production, xylan in feed cannot be effectively degraded, which will significantly reduce digestibility of nutrients in animals, decrease feed intake, and affect the production performance of livestock and poultry. The excretion of viscous feces brings difficulties to health control, leading to an increase in the incidence in livestock and poultry. In addition, it can also affect the deposition of pigments in eggs of poultry, and make meat poultry carcasses whiter, thereby reducing the level of the carcasses.

Xylanase refers to the general term for enzymes that can degrade xylan into xylo-oligosaccharides and xylose, which mainly includes endo β-1,4-xylanase, xylosidase, arabinosidase, etc. Among them, endo-β-1,4-xylanase plays a major role. There are many kinds of microorganisms that produce xylanase: filamentous fungi, bacteria, actinomycetes, etc. According to research reports, the bacteria that produce xylanase mainly include *Bacillus subtilis, Clostridium Ther-*

*mocellum, Pseudomonas fluorescens*, etc.; the actinomycetes that produce xylanase mainly include *Streptomyces lilacinus* and *Streptomyces thermoviolaceus*, etc.; the filamentous fungi that produce xylanase mainly include *Aspergillus niger, Aspergillus nidulans, Aspergillus phoenicis, Trichoderma reesei, Trichoderma* Koningi and so on. The current research on xylanase is mainly concentrated on filamentous fungi.

Xylanase has a wide range of industrial applications. In addition to feed field, it can also be used in papermaking, foods, textile and biomass energy. Different application environments in different industries require xylanase to have corresponding enzyme properties. For example, the feed industry needs acid-resistant xylanase, but the paper industry prefers alkaline xylanase. Moreover, in addition to enzyme properties, specific activity is also a key indicator that limits the application of xylanase. As the higher the specific activity of xylanase itself, the lower the production cost and the lower the price of the enzyme, which would be more conducive to promoting its wide application. Therefore, screening out xylanase with high specific activity is also the goal of researchers in the field.

SUMMARY

In view of this, the present disclosure provides a xylanase mutant to obtain mutant protein with improved specific activity, thereby facilitating the wide application of xylanase in the feed field.

In order to achieve the above-mentioned purpose of the present disclosure, the present disclosure provides the following technical solutions.

The present disclosure provides a xylanase mutant comprising an amino acid sequence having at least 90% identity with SEQ ID NO: 1 and having an amino acid substitution in at least one position selected from the group consisting of 78, 143, 148, 163, 177 and 206 compared with SEQ ID NO: 1.

In some embodiments of the present disclosure, the amino acid sequence of the mutant has at least 91%, 92%, 93%, 94%, 95%, 96%, 97%, 98%, or at least 99% identity with SEQ ID NO: 1.

In some more specific embodiments, the amino acid sequence of the mutant has at least 99.1%, 99.2%, 99.3%, 99.4%, 99.5%, 99.6%, 99.7%, 99.8%, or at least 99.9% identity with SEQ ID NO: 1.

In some embodiments of the present disclosure, the mutant comprises at least one amino acid substitution selected from the group consisting of M78F, V143I, R148K, F163W, I177V and V206L.

In some embodiments of the present disclosure, the mutant comprises a substitution or a combination of substitutions selected from the group consisting of:

M78F,
M78F/V143I,
M78F/R148K,
M78F/F163W,
M78F/I177V,
M78F/V206L,
M78F/V143I/R148K,
M78F/V143I/F163W,
M78F/V143I/I177V,
M78F/V143I/V206L,
M78F/R148K/F163W,
M78F/R148K/I177V,
M78F/R148K/V206L,
M78F/F163W/I177V,

M78F/F163W/V206L,
M78F/I177V/V206L,
M78F/V143I/R148K/F163W,
M78F/V143I/R148K/I177V,
M78F/V143I/R148K/V206L,
M78F/V143I/F163W/I177V,
M78F/V143I/F163W/V206L,
M78F/V143I/I177V/V206L,
M78F/R148K/F163W/I177V,
M78F/R148K/F163W/V206L,
M78F/R148K/I177V/V206L,
M78F/F163W/I177V/V206L,
V143I,
V143I/R148K,
V143I/F163W,
V143/I177V,
V143I/V206L,
V143I/R148K/F163W,
V143I/R148K/I177V,
V143I/R148K/V206L,
V143I/F163W/I177V,
V143I/F163W/V206L,
V143I/I177V/V206L,
V143I/R148K/F163W/I177V,
V143I/R148K/F163W/V206L,
V143I/R148K/I177V/V206L,
R148K,
R148K/F163W,
R148K/I177V,
R148K/V206L,
R148K/F163W/I177V,
R148K/F163W/V206L,
R148K/I177V/V206L,
R148K/F163W/I177V/V206L,
F163W,
F163W/I177V,
F163W/V206L,
F163W/I177V/V206L,
I177V,
I177V/V206L,
V206L,
M78F/V143I/R148K/F163W/I177V,
M78F/V143I/R148K/F163W/V206L,
M78F/V143I/R148K/I177V/V206L,
M78F/R148K/F163W/I177V/V206L,
V143I/R148K/F163W/I177V/V206L,
M78F/V143I/F163W/I177V/V206L, and
M78F/V143I/R148K/F163W/I177V/V206L.

The present disclosure also relates to DNA molecules encoding the aforementioned xylanase mutants.

The present disclosure also relates to a recombinant expression vector comprising the above-mentioned DNA molecule.

The present disclosure also relates to a host cell comprising the above-mentioned recombinant expression vector.

By transformation of the above-mentioned expression vector into a host cell, the obtained recombinant xylanase mutant has a significantly improved specific activity.

In some embodiments of the present disclosure, the host cell is *Pichia pastoris*.

The present disclosure also provides a preparation method of the above-mentioned xylanase mutant, comprising:

Step 1: obtaining a DNA molecule encoding a xylanase mutant, the xylanase mutant comprising an amino acid sequence having at least 90% identity with SEQ ID NO: 1 and having an amino acid substitution in at least one position selected from the group consisting of 78, 143, 148, 163, 177 and 206 compared with SEQ ID NO: 1;

Step 2: fusing the DNA molecule obtained in step 1 with an expression vector, constructing a recombinant expression vector, and transforming the vector into a host cell; and Step 3: inducing the host cell containing the recombinant expression vector to express fusion protein, and isolating and purifying the expressed fusion protein.

In some embodiments of the present disclosure, the xylanase mutant described in step 1 contains at least one amino acid substitution selected from the group consisting of M78F, V143I, R148K, F163W, I177V and V206L.

In some embodiments of the present disclosure, the host cell described in step 2 is *Pichia pastoris*.

The present disclosure also provides the uses of the xylanase mutant in feed.

Based on the wild-type xylanase PT, the present disclosure provides a mutant containing at least one mutation among M78F, V143I, R148K, F163W, I177V, and V206L. Compared with xylanase PT, the specific activity of the mutants with single point mutation provided by the present disclosure is generally increased by 12.3-71.1%, and the specific activity of the mutants with combined mutations is generally increased by 84.0-106.4%. The effect is significant, which is beneficial to reduce the production cost of xylanase and promote the wide application of xylanase in feed.

DETAILED DESCRIPTION

The present disclosure discloses xylanase mutants, methods for preparing the same, uses of the same, DNA molecules encoding the xylanase mutants, vectors, and host cells. Those skilled in the art can learn from the content of this application and appropriately improve the process parameters to achieve the present invention. The methods and uses of the present disclosure have been described through the preferred embodiments. It is obvious that relevant persons can modify or appropriately change and combine the methods and applications described herein without departing from the content, spirit and scope of the present disclosure to achieve and apply the technology of the present disclosure.

In the present disclosure, conventional techniques and methods in the fields of genetic engineering and molecular biology are used, such as the methods described in MOLECULAR CLONING: A LABORATORY MANUAL, 3nd Ed. (Sambrook, 2001) and CURRENT PROTOCOLS IN MOLECULAR BIOLOGY (Ausubel, 2003). These general references provide definitions and methods known to those skilled in the art. However, those skilled in the art can use other conventional methods, experimental schemes, and reagents in the field on the basis of the technical solutions described in the present disclosure, and are not limited to the specific embodiments of the present disclosure. For example, the following experimental materials and reagents are used in the present disclosure:

Strains and vectors: *Escherichia coli* DH5α, *Pichia pastoris* GS115, vector pPIC9k, Amp, and G418 were purchased from Invitrogen.

Enzymes and kits: PCR related enzymes and ligases were purchased from Takara, restriction enzymes were purchased from Fermentas, plasmid extraction kits and gel purification recovery kits were purchased from Omega, GeneMorph II random mutagenesis kits were purchased from Beijing Bomax Biotechnology Co., Ltd.

Medium Formulas:

*E. coli* culture medium (LB medium): 0.5% yeast extract, 1% peptone, 1% NaCl, pH 7.0;

Yeast medium (YPD medium): 1% yeast extract, 2% peptone, 2% glucose;

Yeast selective medium (MD medium): 2% peptone, 2% agarose;

BMGY medium: 2% peptone, 1% yeast extract, 100 mM potassium phosphate buffer (pH 6.0), 1.34% YNB, $4 \times 10^{-5}$% biotin, 1% glycerol;

BMMY medium: 2% peptone, 1% yeast extract, 100 mM potassium phosphate buffer (pH 6.0), 1.34% YNB, $4 \times 10^{-5}$% biotin, 0.5% methanol;

LB/Amp medium: 0.5% yeast extract, 1% peptone, 1% NaCl, 100 µg/mL ampicillin, pH 7.0;

LB/Amp plate: 0.5% yeast extract, 1% peptone, 1% NaCl, 1.5% agar, 100 µg/mL ampicillin, pH 7.0.

Hereinafter, the present disclosure is further illustrated by the following examples.

Example 1 Screening of Xylanase Mutants with Improved Specific Activity

The amino acid sequence of the wild-type xylanase PT derived from the eukaryotic Chytrid phylum *Neocallimastix* genus is shown in SEQ ID NO: 1 and the nucleotide sequence coding xylanase PT is shown in SEQ ID NO: 2. In order to improve the specific activity of xylanase PT, a protein structure analysis was conducted. The protein has a half grip structure in the right hand direction which is formed by a folding sheet, and two catalytic residues are located in a crack formed by a highly twisted β-sheet that can accommodate xylan sugar chains. Mutations were introduced into the gene while avoiding destroying the secondary structure and active center of the protein.

1.1 Designing PCR Primers PT-F1 and PT-R1:

PT-F1: GGCGAATTC CAAAGTTTCTGTAGTTCAGCTTCTC (SEQ ID NO: 3) (Underlined sequence is the recognition site of restriction enzyme EcoRI);

PT-R1: ATAGCGGCCGC TTATCATTAATCAC-CAATGTAAACCT (SEQ ID NO: 4) (Underlined sequence is the recognition site of restriction enzyme NotI).

The PT gene (SEQ ID NO: 2) was used as the template, and the above primers were used for PCR amplification with the GeneMorph II Random Mutation PCR Kit (Stratagene). PCR products were recovered by gel purification. The PCR products were digested with EcoRI and NotI and ligated into pET21a vector digested with the same enzymes. After ligation, the pET21a vector was transformed into *E. coli* BL21 (DE3), and the *E. coli* BL21 cells were spread on LB/Amp plate, and the plate was incubated upside down at 37° C. After the transformants appeared, they were picked up one by one to 96-well plates with toothpicks, and 150 µL of LB/Amp medium containing 0.1 mM IPTG was added to each well. After incubating at 37° C., 220 rpm for about 6 hours, the plates were centrifuged and the supernatants were discarded. The bacteria were resuspended in buffer, frozen and thawed repeatedly to break cell wall to obtain *E. coli* cell lysates containing xylanase.

30 µl of lysate was transferred into two new 96-well plates respectively. 30 µl of substrate was added to one of the two plates, reacted at 37° C. for 30 min, and then reducing sugar was determined with DNS method. 150 µl of Coomassie Brilliant Blue solution was added to the other plate, the plate was allowed to stand for 10 minutes, and the protein content was determined by the Coomassie Brilliant Blue binding method (Bradford assay). The enzyme activity and protein content of each mutant were calculated. In the end, from more than 20,000 transformants, the following mutation positions were screened out, which significantly improved the specific activity of PT without affecting its original properties: M78F, V143I, R148K, F163W, I177V and V206L.

On the basis of the wild-type xylanase PT, the present disclosure provides mutants containing single mutation site of M78F, V143I, R148K, F163W, I177V, or V206L, respectively.

The present disclosure also provides xylanase mutants containing at least 2, at least 3, at least 4, at least 5, and at least 6 mutation sites selected from the group consisting of M78F, V143I, R148K, F163W, I177V and V206L. For example, mutants with two point mutations: M78F/F163W, V143I/I177V, F163W/I177V, M78F/R148K, R148K/V206L, R148K/F163W, I177V/V206L; mutants with three point mutations: M78F/V143I/F163W, M78F/F163W/I177V, M78F/R148K/F163W, V143I/R148K/V206L, R148K/F163W/V206L; mutants with four point mutations: M78F/V143I/R148K/F163W, M78F/F163W/I177V/V206L, V143I/R148K/F163W/V206L, V143I/F163W/I177V/V206L, R148K/F163W/I177V/V206L; mutants with five point mutations: M78F/V143I/R148K/F163W/V206L, M78F/V143I/F163W/I177V/V206L, and mutants with six point mutations: M78F/V143I/R148K/F163W/I177V/V206L.

Example 2 Expression of Xylanase Mutants in *Pichia pastoris*

According to the codon preference of *Pichia pastoris*, the gene sequence of PT (SEQ ID NO: 2) and the sequences of the above-mentioned mutants were optimized and synthesized, and EcoRI and NotI restriction sites were respectively added to the 5' and 3'ends of the synthesized sequences.

2.1 Construction of Expression Vector

The synthesized gene sequences of PT and the mutants were digested with EcoRI and NotI respectively, and then ligated into the pPIC-9K vector digested with the same enzymes, at 16° C. overnight. The ligation products were transformed into *E. coli* DH5a, and the *E. coli* DH5a cells were spread on the LB/Amp plate, and the plate was incubated upside down at 37° C. After the colonies appeared, colony PCR (reaction system: single colony picked from the plate as template, rTaqDNA polymerase 0.5 µl, 10×Buffer 2.0 µl, dNTPs (2.5 mM) 2.0 µl, 5'AOX primer (10 mM) 0.5 µl, 3'AOX primer 0.5 µl, ddH₂O 14.5 µl; reaction program: 95° C. pre-denaturation 5 min; 30 cycles: 94° C. 30 sec, 55° C. 30 sec, 72° C. 2 min; 72° C. 10 min) was performed to verify positive colonies. After sequencing verification, the correct recombinant expression plasmids were obtained.

2.2 Construction of *Pichia pastoris* Engineering Strain 2.2.1 Preparation of Yeast Competent Cells The *Pichia pastoris* GS115 strain was activated on YPD plate. After being cultured at 30° C. for 48 hours, single colony of activated GS115 was inoculated into 6 mL of YPD liquid medium and cultured at 30° C., 220 rpm for about 12 hours. The culture broth was transferred into a triangular flask containing 30 ml of YPD liquid medium, cultured at 30° C., 220 rpm for about 5 hours. The cell density was detected by UV spectrophotometer. After the OD600 value was in the range of 1.1-1.3, 4 mL of the culture broth was aliquoted into a sterilized EP tube and centrifuged at 4° C., 9,000 rpm for 2 min. The supernatant was discarded, and the remaining supernatant was removed by sterile filter paper. The cells were suspended in 1 mL of pre-cooled sterilized water, and centrifuged at 4° C., 9,000 rpm for 2 min. The supernatant was discarded gently and the cells were washed with 1 mL sterile water again, centrifuged at 4° C., 9,000 rpm for 2 min, the supernatant was discarded gently. Then the yeast cells were suspended in 1 mL of pre-cooled sorbitol (1 mol/L), centrifuged at 4° C., 9,000 rpm for 2 min, and the supernatant was discarded gently. The cells were suspended gently in 100-150 µl of pre-cooled sorbitol (1 mol/L).

2.2.2 Transformation and Screening

The expression plasmids constructed in 2.1 were linearized with Sac I. The linearized fragments were purified, recovered and transformed into *Pichia pastoris* GS115 by electroporation. The *Pichia pastoris* recombinant strains were screened on MD plates, and the transformants with multiple copies were screened on YPD plates containing different concentrations of G418 (0.5 mg/mL-8 mg/mL).

The obtained transformants were transferred to BMGY medium and cultured with shaking at 30° C. and 250 rpm for 1d; then transferred to BMMY medium and cultured with shaking at 30° C. and 250 rpm. 0.5% methanol was added every day to induce expression for 4 days. The broths were centrifuged at 9,000 rpm for 10 min to remove the yeasts, fermentation supernatants containing wild-type xylanase PT and xylanase mutants were obtained respectively.

According to the above method, the recombinant *Pichia pastoris* engineering strains expressing wild-type xylanase PT and xylanase mutants were constructed and obtained respectively.

2.3 Determination of Xylanase Activity (1) Definition of Enzyme Activity Unit

Under the conditions of 37° C. and pH 5.5, the amount of enzyme required to release 1 µmol reducing sugar from 5 mg/ml xylan solution per minute is defined as one enzyme activity unit U.

(2) Method for Determining Xylanase Activity 2 ml of 1% xylan substrate (prepared with acetic acid-sodium acetate buffer, pH 5.5) was added to the colorimetric tube, equilibrated at 37° C. for 10 min, then 2 ml of acidic xylanase solution which was properly diluted by acetic acid-sodium acetate buffer (pH 5.5) and equilibrated at 37° C. was added, and mixed well and incubated at exact 37° C. for reaction for 30 min. After the reaction was over, 5 ml of DNS reagent was added and mixed well to stop the reaction. The mixture was boiled in a boiling water bath for 5 minutes, cooled to room temperature with tap water, and distilled water was added to make the volume up to 25 ml. After mixing, the absorbance AE at 540 nm was measured by using the standard blank as a blank control.

Calculation Formula of Enzyme Activity:

$$X_D = \frac{[(A_E - A_B) \times K + C_0]}{M \times t} \times N \times 1000;$$

Wherein: $X_D$ is the activity of xylanase in the diluted enzyme solution, U/ml; $A_E$ is the absorbance of the enzyme reaction solution; $A_B$ is the absorbance of the enzyme blank solution; K is the slope of the standard curve; $C_0$ is the intercept of the standard curve; M is the molar mass of xylose, 150.2 g/mol; t is the enzymatic hydrolysis reaction time, min; N is the dilution factor of the enzyme solution; 1000 is the conversion factor, 1 mmol=1000 µmol.

(3) Results of Enzyme Activity Determination

The xylanase activity in the fermentation supernatant from the *Pichia pastoris* engineering bacteria was detected according to the above method. The results showed that the enzyme activity of the fermentation supernatants from the recombinant *Pichia pastoris* engineering strains expressing wild-type xylanase PT or mutants was 180-400 U/mL.

2.4 Determination of Protein Content (1) Methods

Coomassie Brilliant Blue binding method (Bradford assay) is a method combining colorimetric method and pigment method to determine protein content. Coomassie Brilliant Blue G-250 is brownish-red in acidic solution, and turns blue when binds to protein. The color change conforms to Beer's law within a certain concentration range of protein, and can be measured by colorimetry at 595 nm. It can be absorbed in a large amount within 3 to 5 minutes and is stable for at least 1 hour. The absorbance is directly proportional to the protein concentration within the range of 10-1000 ug/mL.

The enzyme solution and Coomassie Brilliant Blue solution were mixed at a volume ratio of 1:5, and left to stand for 10 minutes. The protein content was determined by the Coomassie Brilliant Blue method (Bradford assay).

(2) Results of Protein Content Determination

The xylanase protein content in the fermentation supernatants of the above-mentioned *Pichia pastoris* engineering strains were detected according to the above method. The results showed that the protein content of the fermentation supernatant of the recombinant *Pichia pastoris* engineering strain expressing wild-type xylanase PT or mutants was 0.04-0.1 mg/mL.

2.5 Calculation of Specific Activity

"Specific Activity" refers to the number of enzyme activity units in a unit weight of protein, generally expressed in U/mg protein. Generally speaking, the higher the specific activity of the enzyme, the purer the enzyme.

Calculation formula of specific activity: specific activity (U/mg)=enzyme activity (U/mL)/protein content (mg/mL).

The specific activity of xylanase in the fermentation supernatant of the recombinant *Pichia pastoris* engineering strain expressing wild-type xylanase PT or mutants was calculated respectively.

The calculation results show that compared with the wild-type xylanase PT, the specific activity of the xylanase mutants containing single mutation site of M78F, V143I, R148K, F163W, I177V, and V206L is increased by 24.8%, 25.6%, 66.6%, 12.3%, 63.1%, and 71.1% respectively. This shows that the specific activity of the mutants with single mutation provided by the present disclosure on the basis of wild-type xylanase PT is significantly improved.

In addition, the present disclosure provides xylanase mutants comprising a combination of any two or more mutation sites selected from the group consisting of M78F, V143I, R148K, F163W, I177V, and V206L, such as mutants with two point mutations: M78F/F163W, V143I/I177V, F163W/I177V, M78F/R148K, R148K/V206L, R148K/F163W, I177V/V206L; mutants with three point mutations: M78F/V143I/F163W, M78F/F163W/I177V, M78F/R148K/F163W, V143I/R148K/V206L, R148K/F163W/V206L; mutants with four point mutations: M78F/V143I/R148K/F163W, M78F/F163W/I177V/V206L, V143I/R148K/F163W/V206L, V143I/F163W/I177V/V206L, R148K/F163W/I177V/V206L; mutants with five-point mutants:

M78F/V143I/R148K/F163W/V206L, M78F/V143I/ F163W/I177V/V206L; and mutant with six point mutations: M78F/V143I/R148K/F163W/I177V/V206L. Their specific activity is generally increased by 84.0%-106.4%, significantly higher than the specific activity of the above-mentioned mutants with single point mutation. Therefore, an unexpected technical effect is achieved by the present disclosure.

The invention claimed is:

1. A xylanase mutant, wherein the mutant comprises an amino acid sequence having at least 90% identity with SEQ ID NO: 1, and having an amino acid substitution of V143I and an amino acid substitution of I177V, compared with SEQ ID NO: 1.

2. The xylanase mutant of claim 1, wherein the amino acid sequence of the mutant has at least 91%, 92%, 93%, 94%, 95%, 96%, 97%, 98%, or at least 99% identity with SEQ ID NO: 1.

3. The xylanase mutant of claim 1, wherein the amino acid sequence of the mutant has at least 99.1% identity with SEQ ID NO: 1.

4. The xylanase mutant of claim 1, wherein the mutant further comprises at least one amino acid substitution selected from the group consisting of M78F, R148K, F163W and V206L.

5. The xylanase mutant of claim 1, wherein the mutant comprises a combination of substitutions selected from the group consisting of:

M78F/V143I/I177V,
M78F/V143I/R148K/I177V,
M78F/V143I/F163W/I177V,
M78F/V143I/I177V/V206L,
V143I/R148K/I177V,
V143I/F163W/I177V,
V143I/I177V/V206L,
V143I/R148K/F163W/I177V,
V143I/R148K/I177V/V206L,
M78F/V143I/R148K/F163W/I177V,
M78F/V143I/R148K/I177V/V206L,
V143I/R148K/F163W/I177V/V206L,
M78F/V143I/F163W/I177V/V206L, and
M78F/V143I/R148K/F163W/I177V/V206L.

6. A DNA molecule encoding the xylanase mutant of claim 1.

7. A recombinant expression vector comprising the DNA molecule of claim 6.

8. A host cell transformed with the recombinant expression vector of claim 7.

9. The host cell of claim 8, wherein the host cell is *Pichia pastoris*.

* * * * *